US012748095B2

(12) United States Patent
Yao et al.

(10) Patent No.: US 12,748,095 B2
(45) Date of Patent: Sep. 29, 2026

(54) APPARATUS AND TECHNIQUE FOR SIMULATING THE PROPAGATION OF SHALE FRACTURES UNDER HIGH TEMPERATURE CONVECTIVE HEAT

(71) Applicant: China University of Petroleum (East China), Qingdao (CN)

(72) Inventors: Chuanjin Yao, Qingdao (CN); Jiao Ge, Qingdao (CN); Junwei Hu, Qingdao (CN); Liang Xu, Qingdao (CN); Qi Zhang, Qingdao (CN); Lei Li, Qingdao (CN); Kai Zhang, Qingdao (CN); Jianchun Xu, Qingdao (CN)

(73) Assignee: China University of Petroleum (East China), Qingdao (CN)

( * ) Notice: Subject to any disclaimer, the term of this patent is extended or adjusted under 35 U.S.C. 154(b) by 940 days.

(21) Appl. No.: 18/149,945

(22) Filed: Jan. 4, 2023

(65) Prior Publication Data

US 2023/0366304 A1 Nov. 16, 2023

(30) Foreign Application Priority Data

May 16, 2022 (CN) ........................ 202210526058.4

(51) Int. Cl.
*G01N 33/24* (2006.01)

(52) U.S. Cl.
CPC .......... *G01N 33/24* (2013.01); *E21B 2200/20* (2020.05); *G01N 2203/0067* (2013.01); *G01V 2210/646* (2013.01)

(58) Field of Classification Search
CPC ............ G01N 33/24; G01N 2203/0067; E21B 2200/20; G01V 2210/646
See application file for complete search history.

(56) References Cited

FOREIGN PATENT DOCUMENTS

| | | | | |
|---|---|---|---|---|
| CN | 109870743 A | * | 6/2019 | |
| CN | 110005392 A | | 7/2019 | |
| CN | 113008686 A | * | 6/2021 | .......... G01N 15/082 |
| CN | 113670778 A | * | 11/2021 | ............ G01N 13/04 |

* cited by examiner

*Primary Examiner* — Crystal J Lee
(74) *Attorney, Agent, or Firm* — Nitin Kaushik

(57) ABSTRACT

The invention relates to the technical field of in-situ development of shale oil resources and consists of a device and technique for simulating the propagation of shale fractures under the influence of high-temperature convective heat. The apparatus is comprised of a data collecting and processing system, a high-temperature thermal fluid generator, a high-pressure pumping device, and a shale reactor. The thermal fluid generator for high temperatures consists of a fluid generator, a temperature controller, and a pressure controller. The shale, reaction kettle consists of an outer chamber, an outer chamber lid, a scaled rock cavity, and a shale sample. The outer cavity cover of the reactor is fitted with a simulated wellbore, the bottom end of the simulated wellbore penetrates the inner cavity cover and extends to the interior of the shale sample, and the top of the simulated wellbore is connected to a high-pressure constant-speed injection pump.

7 Claims, 3 Drawing Sheets

APPARATUS AND TECHNIQUE FOR SIMULATING THE PROPAGATION OF SHALE FRACTURES UNDER HIGH TEMPERATURE CONVECTIVE HEAT

CROSS-REFERENCE TO RELATED APPLICATIONS

The application claims priority to Chinese patent application No. 2022105260584, filed on May 16, 2022, the entire contents of which are incorporated herein by reference.

TECHNICAL FIELD

The current invention pertains to the area of in-situ development of shale oil resources. It applies specifically to an apparatus and technique for simulating the propagation of shale fractures under high temperature convective heat.

BACKGROUND

The development of shale oil resources has heroine an essential subject for the strategic development of future energy supplies. It is crucial to resolve the disparity between oil and gas production and demand, lessen reliance on imported oil, and maintain national energy security. Currently, shale oil resources are characterized by a considerable burial depth, limited matrix permeability, and low oil production. In recent years, the underground in-situ heating conversion mining technology that is the subject of domestic and international research has been regarded as a mining technology that can effectively produce shale oil resources. In other words, the shale reservoir is heated to a high temperature in order to convert the unconverted organic matter kerogen into light oil and natural gas on a massive scale, as well as convert the remaining heavy hydrocarbons into light hydrocarbons. In addition, it is expelled via the pores and fractures created by high temperature and retrieved from the earth using conventional oil extraction methods. Among these, thermal fluid convective heating is an efficient technology for shale oil recovery that has gained considerable interest from business and academics owing to its benefits, which include excellent oil quality, a high rate of recovery, safety and environmental protection.

However, during the in-situ transformation kind development of shale, the issue of property change at high temperatures is inescapable. The temperature fluctuation and temperature gradient induced by high temperature will produce thermal stress, which will result in the commencement and growth of fractures. Thermal damage has a major impact on rock fracture propagation. Under the influence of high-temperature and high-pressure thermal fluids, even a little change in thermal conditions will have a direct impact on the fracture pressure, fracture route, and ultimate fracture morphology of shale reservoirs. The majority of extant numerical simulation studies simplify, the solution to the in-situ conversion issue, which is inconsistent with real ground conditions and lacks experimental verification. Real shale samples may be utilized to more intuitively examine the shale fracture propagation process under the influence of high-temperature convective heat, thanks to laboratory test research that recreates the subterranean in-situ circumstances in the actual engineering backdrop.

Therefore, it is required to investigate the process of high-temperature convective thermal fracturing and the mechanism of shale fracture propagation by analyzing the evolution features of micro-cracks in shale reservoirs under the influence of thermal fluid. Clarify the major mechanism of fracture propagation in shale reservoirs under the influence of thermal fluid and the fracture morphology change law. Therefore, it gives significant theoretical advice for the optimization and adjustment of heating parameters of high-temperature high-pressure thermal fluids.

SUMMARY

Example of the present invention includes an apparatus and technique for simulating the propagation of shale fractures under high temperature convective heat. This experimental technology can imitate and replicate conditions underground. The experimental investigation on the fracturing of shale by the action of a high-temperature and high-pressure thermal fluid was conducted on genuine shale samples under realistic reservoir conditions. During the experiment, constant monitoring of the reactor temperature, heating rate, triaxial confining pressure, thermal fluid injection pressure, and injection rate. Through post-processing observation and analysis of experimental rock samples, the primary regulating variables influencing fracture morphology are elucidated. Finally, the mechanism of shale fracture development and propagation triggered by high-temperature high-pressure fluid is revealed. In order to give theoretical and technical assistance for the development of shale oil resources on a large scale.

In light of the aforementioned issues, the current invention proposes the following technological solution:

The invention relates to an apparatus for simulating the propagation of shale fractures under high temperature convective heat, including a data collecting and processing system, a high-temperature thermal fluid generator, a high-pressure pumping device and a shale reaction kettle. High temperature thermal fluid generator comprises fluid generator, temperature controller, and pressure controller. Both the output ends of the temperature controller and the pressure controller are linked electrically to the input end of the fluid generator. High-pressure pumping device comprises a high-pressure constant-speed injection pump and a high-pressure constant-speed injection pump controller Electrically connecting the output end of the high-pressure constant-speed injection pump controller to the input end of the high-pressure constant-speed injection pump. The output end of the data collecting and processing system is electrically coupled to the input end of the high-pressure constant-speed injection pump controller. Shale reaction kettle consists of a reaction kettle outer chamber, a reaction kettle outer cavity cover, a rock sealed cavity, and a shale sample. The reaction kettle outer chamber cover is positioned atop the reaction kettle outer chamber, and the rock sealed cavity is embedded in the reaction kettle outer chamber. The shale sample is positioned within the rock sealed cavity, and the inner net size of the rock sealed cavity is the same as the external size of the shale sample. A reaction kettle inner cavity cover is positioned over the rock sealed cavity, and fastening bolts are positioned atop the reaction kettle inner cavity cover. The fastening bolts are screwed to the top of the rock sealed cavity. A reaction kettle base is provided at the bottom of the reaction kettle outer chamber. A simulated wellbore is placed on the reaction kettle outer chamber cover, and the bottom end of the simulated wellbore extends through the reaction kettle inner cavity cover to the shale sample. The top of the simulated wellbore communicates with the high-pressure constant-speed injection pump.

As a preferable technical solution of the present invention, the output end of the fluid generator is equipped with a connecting pipe. The other end of the connecting pipe is connected to the intake end of the high-pressure constant-speed injection pump, and the connecting pipe is equipped with an injection valve.

As a preferable technical solution of the present invention, the outlet end of the high-pressure constant-speed injection pump is linked to a high-pressure pump injection pipe. On top of the simulated wellbore is a thread, and the other end of the high-pressure pump injection pipe is threadedly attached to the thread. The high-pressure pump injection pipe is equipped with an injection valve, an injection fluid pressure detector, and an injection fluid temperature detector. Both the output ends of the injection fluid pressure detector and the injection fluid temperature detector are linked electrically to the input end of the data collection and processing system, and the injection fluid pressure detector is equipped with a first safety valve.

As a preferable technical solution of the present invention, the left side, the right side, and the bottom side of the reaction kettle outer chamber are respectively-provided with an X-axis confining pressure loader, a Y-axis confining pressure loader, and a Z-axis confining pressure loader. The telescoping ends of the X-axis confining pressure loader, the Y-axis confining pressure loader, and the Z-axis confining pressure loader are in contact with the shale sample and penetrate the side wall of the rock sealed cavity. The output ends of the X-axis confining pressure loader, Y-axis confining pressure loader, and Z-axis confining pressure loader are electrically connected to the X-axis confining pressure detector, Y-axis confining pressure detector, and Z-axis confining pressure detector, respectively. The X-axis confining pressure detector has a second safety valve, the Y-axis confining pressure detector has a third safety valve, and the Z-axis confining pressure detector has a fourth safety valve. The terminal electrical connection between the input end of the X-axis confining pressure loader, the Y-axis confining pressure loader, and the Z-axis confining pressure loader, as well as the output of the data collecting and processing system. Electrical connection is made between the output terminals of the X-axis confining pressure detector, the Y-axis confining pressure detector, and the Z-axis confining pressure detector, and the input terminal of the data collecting and processing system.

As a preferable technical solution of the present invention, the inner wall of the rock sealed cavity is equipped with a reactor temperature controller and a reactor temperature detector. Electrically connecting the input end of the reactor temperature controller to the output end of the data collecting and processing system. The output end of the reactor temperature detector is electrically linked to the input end of the data collection and processing system.

As a preferable technical solution of the present invention, wherein the data collecting and processing system comprises a computer, a data collecting module, and a data processing module. The computer is employed for the operation and management of the whole experiment. The data collecting module is used for real-time observation, simultaneous data collection, and experimental data display. The data processing module is used for final data processing, export, and experiment storage.

Alternatively, an experimental approach for simulating, the propagation of shale fractures under the influence of high-temperature convective heat including the stages of:

S1, specimen preparation. A 100 mm×100 mm×100 mm typical shale sample was prepared and drilled using a bench drill. The pre-processed simulated wellbore is put into the shale sample, and epoxy resin glue is used for fixing and sealing.

S2, device construction. The shale sample with the simulated wellbore installed is put in the rock sealed cavity, followed by the sequential installation of the reaction kettle inner cavity cover and reaction kettle outer cavity cover. The data collecting and processing system, the high-temperature thermal fluid generator, the high-pressure pump injection device and the shale reaction kettle's valves and pipes are then installed and linked.

S3, modeling of in situ formation circumstances. The parameters of the reactor temperature controller and the reactor triaxial confining pressure loader are set on the computer based on the required temperature and confining pressure of the experimental research, allowing the shale reaction kettle to simulate and realize the in-situ conditions of the formation. By connecting the reactor temperature detector and the reactor triaxial confining pressure detector to the data collecting module, the real-time experimental conditions of the reactor are monitored, the detection data is transmitted to the data collecting and processing system, and the data processing module records all relevant experimental data.

S4, high temperature thermal fluid generator setting. Configure the temperature controller and pressure controller in order for the fluid generator to create the thermal fluid conditions necessary for experimental research.

S5, high-pressure pumping device setting. A high-pressure constant-speed injection pump controller regulates the injection flow rate and injection pressure of the high-temperature and high-pressure thermal fluid. Turn on the high-pressure constant-speed injection pump to inject thermal fluid at a high temperature. During the experiment, the injection fluid temperature detector measures the injection temperature in real time. The injection fluid pressure detector monitors the injection pressure in real time during the experiment and communicates the detection data to the data collecting and processing system, where the data processing module captures and stores the pressure data.

S6, outputting experimental data. Draw the temperature and pressure change curves over time using the temperature and pressure values acquired by the data collecting and processing system. Data storage and export for post-processing analysis.

S7, removing the sample. Unload the triaxial confining pressure loader at completion of the experiment. Close the reactor temperature controller, the fluid generator, and the high-pressure constant-speed injection pump. Remove the shale sample once it has cooled.

S8, analyzing the sample for fracture development. Observe and assess the macroscopic fractures that have developed on the surface of the shale sample. Through CT scanning, the three-dimensional spatial distribution of fractures inside the rock sample was determined, and the fracture propagation pattern within the shale was seen.

Compared to previous art, the advantageous result of the present invention is: simulating and achieving in the laboratory the propagation of shale fractures under the action of high-temperature high-pressure thermal fluid under the in-situ circumstances of actual shale reservoirs underneath. The following were constructed: a data collecting and processing system, a high-temperature thermal fluid generator, a high-pressure pumping device, and a shale reaction kettle. Shale samples with varying rock qualities were constructed, and the underground in situ experiment of shale fracture propagation triggered by high-temperature and high-pressure fluids under various circumstances was conducted. Monitoring, recording, and quantitative analysis in real time of injection pressure, displacement, and shale temperature. By installing the data collecting and processing system, control and monitoring of all experiments, as well as the export and storage of experimental data, are accomplished. Setting up a high-temperature thermal fluid generator allows for the real-time control and monitoring of fluids with distinct characteristics. By configuring a high-pressure pumping device, real-time control and monitoring of injected fluids under diverse situations may be accomplished. By configuring the shale reaction kettle, the temperature and pressure of the shale environment may be monitored and controlled in real time. The apparatus is inexpensive, takes up little space, is simple and secure to use, and uses less resources. It is capable of simulating the in-situ condition of the real shale reservoir, the measurement data is precise, and the engineering practice is robust. It is an apparatus and technique for conducting realistic in-situ high-temperature convective heating simulation experiments for shale fracture propagation.

The description provided above is only a summary of the technological solution of the present invention. In order to better comprehend the technological methods of the current invention, it may be executed in accordance with its description. And to make the aforementioned and other objectives, characteristics, and benefits of the present invention more understandable, the precise embodiments of the present invention are detailed below.

BRIEF DESCRIPTION OF DRAWINGS

The structure of an apparatus for simulating shale fracture propagation under the influence of high-temperature convective heat is shown in FIG. 1 of the present invention.

The technique described by the present invention for simulating shale fracture propagation under the influence of high-temperature convective heat is shown in FIG. 2.

Figure 3:
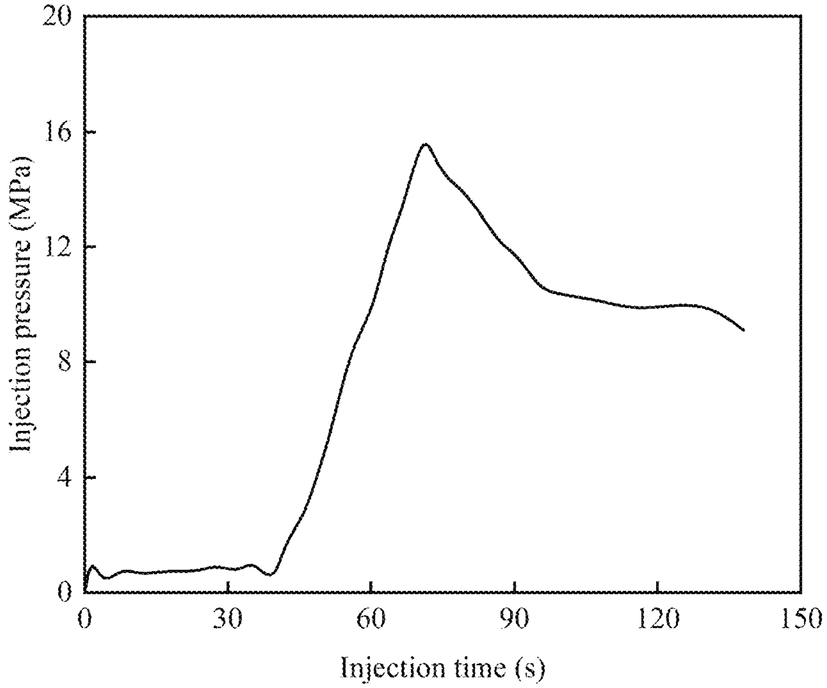

The curve of fluid injection pressure vs time as disclosed by the present invention is shown in FIG. 3.

DESCRIPTION OF DIRECTIONAL INDICATORS

1. data collecting and processing system; 3. high-temperature thermal fluid generator: 4. pressure controller; 5. temperature controller; 6. fluid generator: 8. injection valve; 9. connecting pipe; 10. high-pressure constant-speed injection pump controller; 11. high-pressure pumping device; 12. high-pressure constant-speed injection pump; 13. injection valve; 14. high-pressure pump injection pipe; 15. injection fluid pressure detector; 16. first safety valve; 17. injection fluid temperature detector; 18. thread; 19. simulated wellbore; 20. reaction kettle outer cavity cover; 21. reaction kettle inner cavity cover; 22. fastening bolts; 23. shale reaction kettle; 24. X-axis confining pressure loader; 25. second safety valve; 26. X-axis confining pressure detector; 27. reactor temperature controller; 28. reactor temperature detector; 29. Y-axis confining pressure loader; 30. Y-axial confining pressure detector; 31. third safety valve; 32. shale sample; 33. rock sealed cavity; 34. Z-axial confining pressure loader; 35. Z-axial confining pressure detector; 36. fourth safety valve; 37. reaction kettle outer chamber; 38. reaction kettle base.

DETAILED DESCRIPTION OF THE EMBODIMENTS

In order to clarify the objective, technological solutions, and benefits of the embodiments of the present invention, the technical solutions in the embodiments of the present invention will be described in detail and with clarity below in connection with the accompanying drawings. Evidently, the stated embodiments constitute a subset of the embodiments of the present invention and not all of them. Based on the implementation methods in the present invention, all alternative implementation methods produced by those with ordinary ability in the art without creative effort come within the scope of protection for the present invention.

In light of this, the following extensive explanation of the embodiments of the invention presented in the accompanying figures is not meant to restrict the scope of the claimed invention, but rather depicts chosen embodiments of the invention. Based on the implementation methods in the present invention, all alternative implementation methods produced by those with ordinary ability in the art without creative effort come within the scope of protection for the present invention.

In the following figures, same numbers and letters signify identical objects. Therefore, after an object has been specified in one figure, it is no longer necessary to describe and explain it in future figures.

In describing the present invention, it should be understood that the terms “center”, “’longitudinal”, “transverse”, “length”, “width”, “thickness”, “upper”, “lower”, “front”, “back”, “left”, “right”, “vertical”, “horizontal”, “top”, “bottom”, “inner”, “outer”, “clockwise”, “counterclockwise”, etc., indicated the orientation or positional connection is determined by the orientation or positioning relationship shown in the drawings. It is just for the purpose of explaining the present invention and simplifying the description, and does not suggest or imply that the device or element referred to must have a certain orientation, be manufactured and function in a particular orientation. Consequently, it should not be interpreted as restricting the innovation.

Moreover, the words “first” and “second” are used for descriptive reasons only and cannot be understood as showing or implying relative significance or as implicitly determining the number of mentioned technical qualities. Thus, a trait labeled as “first” or “second” may expressly or implicitly incorporate one or more of these characteristics. Unless otherwise specified, “plurality” throughout the description of the present invention refers to two or more.

Embodiment One

As illustrated in the accompanying drawing 1, the present invention provides a technical scheme: an apparatus for simulating the propagation of shale fractures under high temperature convective heat, characterized in that, including a data collecting and processing system 1, a high-temperature thermal fluid generator 3, a high-pressure pumping device 11 and a shale reaction kettle 23. High temperature thermal fluid generator 3 comprises fluid generator 6, temperature controller 5, and pressure controller 4. Both the output ends of the temperature controller 5 and the pressure controller 4 are linked electrically to the input end of the fluid generator 6. The temperature controller 5 is used to regulate the temperature of the experimental fluid. The pressure controller 4 is paired with the temperature controller 5 to regulate fluids with varying characteristics necessary for the experiment. The fluid generator 6 is used for producing experiments requiring fluid. High-pressure pumping device 11 comprises a high-pressure constant-speed injection pump 12 and a high-pressure constant-speed injection pump controller 10. Electrically connecting the output end of the high-pressure constant-speed injection pump controller 10 to the input end of the high-pressure constant-speed injection pump 12. The output end of the data collecting and processing system is electrically coupled to the input end of the high-pressure constant-speed injection pump controller 1. Shale reaction kettle 23 consists of a reaction kettle outer chamber 37, a reaction kettle outer cavity cover 20, a rock sealed cavity 33, and a shale sample 32. The reaction kettle outer chamber cover 20 is positioned atop the reaction kettle outer chamber 37, and the rock sealed cavity 33 is embedded in the reaction kettle outer chamber 37. The shale sample 32 is positioned within the rock sealed cavity 33, and the inner net size of the rock sealed cavity 33 is the same as the external size of the shale sample 32. A reaction kettle inner cavity cover 21 is positioned over the rock sealed cavity 33, and fastening bolts 22 are positioned atop the reaction kettle inner cavity cover 21. The fastening bolts 22 are screwed to the top of the rock sealed cavity 33. A reaction kettle base 38 is provided at the bottom of the reaction kettle outer chamber 37. A simulated wellbore 19 is placed on the reaction kettle outer chamber cover 20, and the bottom end of the simulated wellbore 19 extends through the reaction kettle inner cavity cover 21 to the shale sample 32. The top of the simulated wellbore 19 communicates with the high-pressure constant-speed injection pump 12. The high-pressure pump injection pipe 14 is preconnected to the simulated wellbore 19 and positioned inside the shale sample 32. The high-temperature thermal fluid is injected at a constant pressure and constant speed into the shale sample 32 using the high-pressure constant-speed injection pump 12. In the shale reaction kettle 23, the rock fracturing experiment was replicated by the convective action of a high-temperature, high-pressure thermal fluid under in-situ subterranean circumstances.

The following technological solutions may also be used to execute embodiments of the present invention.

In accordance with one embodiment of the present invention, the output end of the fluid generator 6 is equipped with a connecting pipe 9. The other end of the connecting pipe 9 is connected to the intake end of the high-pressure constant-speed injection pump 12, and the connecting pipe 9 is equipped with an injection valve 8. Through the connecting pipe 9, the high-temperature thermal fluid is delivered to the high-pressure constant-speed injection pump 12.

In accordance with one embodiment of the present invention, the outlet end of the high-pressure constant-speed injection pump 12 is linked to a high-pressure pump injection pipe 14. On top of the simulated wellbore 19 is a thread 18, and the other end of the high-pressure pump injection pipe 14 is threadedly attached to the thread 18. The high-pressure pump injection pipe 14 is equipped with an injection valve 13, an injection fluid pressure detector 15, and an injection fluid temperature detector 17. Both the output ends of the injection fluid pressure detector 15 and the injection fluid temperature detector 17 are linked electrically to the input end of the data collection and processing system 1, and the injection fluid pressure detector 15 is equipped with a first safety valve 16. The injection fluid temperature detector 17 is used to monitor and show the temperature of the injected fluid in real time. The injection fluid pressure detector 15 monitors the injection flow pressure of the high-pressure constant-speed injection pump 12, as well as the natural fracture closure and initiation process of the shale sample 32.

In accordance with one embodiment of the present invention, the left side, the right side, and the bottom side of the reaction kettle outer chamber 37 are respectively provided with an X-axis confining pressure loader 24, a Y-axis confining pressure loader 29, and a Z-axis confining pressure loader 34. The telescoping ends of the X-axis confining pressure loader 24, the Y-axis confining pressure loader 29, and the Z-axis confining pressure loader 34 are in contact with the shale sample and penetrate the side wall of the rock sealed cavity 33. The output ends of the X-axis confining pressure loader 24. Y-axis confining pressure loader 29, and Z-axis confining pressure loader 34 are electrically connected to the X-axis confining pressure detector 26, Y-axis confining pressure detector 30, and Z-axis confining pressure detector 35, respectively. The X-axis confining pressure detector 26 has a second safety valve 25, the Y-axis confining pressure detector 30 has a third safety valve 31, and the Z-axis confining pressure detector 35 has a fourth safety valve 36. The terminal electrical connection between the input end of the X-axis confining pressure loader 24, the Y-axis confining pressure loader 29, and the Z-axis confining pressure loader 34, as well as the output of the data collecting and processing system 1. Electrical connection is made between the output terminals of the X-axis confining pressure detector 26, the Y-axis confining pressure detector 30, and the Z-axis confining pressure detector 35, and the input terminal of the data collecting and processing system 1. The reactor triaxial confining pressure loader applies triaxial confining pressure loading to the surface of shale sample 32. Using the triaxial confining pressure detector, transfer the confining pressure data to the data collecting and processing system 1 in real time. This guarantees that subsurface conditions in situ are reached.

In accordance with one embodiment of the present invention, the inner wall of the rock sealed cavity 33 is equipped with a reactor temperature controller 27 and a reactor temperature detector 28. Electrically connecting the input end of the reactor temperature controller 27 to the output end of the data collecting and processing system 1. The output end of the reactor temperature detector 28 is electrically linked to the input end of the data collection and processing system 1. The reactor temperature controller 27 warms the rock sealed cavity 33. Temperature heating rate may be set in real time by the reactor temperature controller 27. The reactor temperature detector 2 sends the rock sealed cavity temperature in real time to the data collecting and processing system 1. Timely monitoring and adjustment of the rock airtight cavity's temperature.

In accordance with one embodiment of the present invention, wherein the data collecting and processing system 1 comprises a computer, a data collecting module, and a data processing module. The computer is employed for the operation and management of the whole experiment. The data collecting module is used for real-time observation, simultaneous data collection, and experimental data display. The data processing module is used for final data processing, export, and experiment storage.

Embodiment Two

Figure 1:
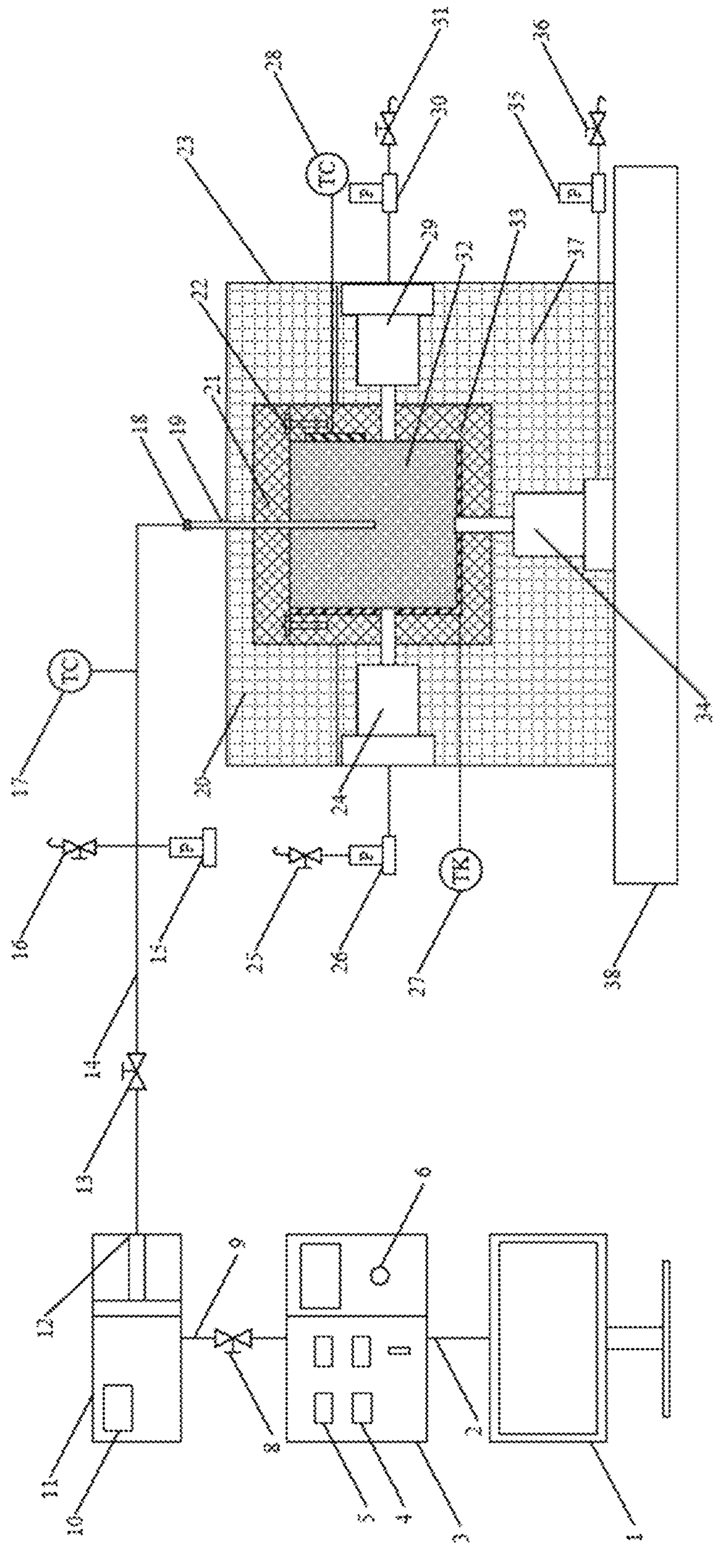
Figure 2:
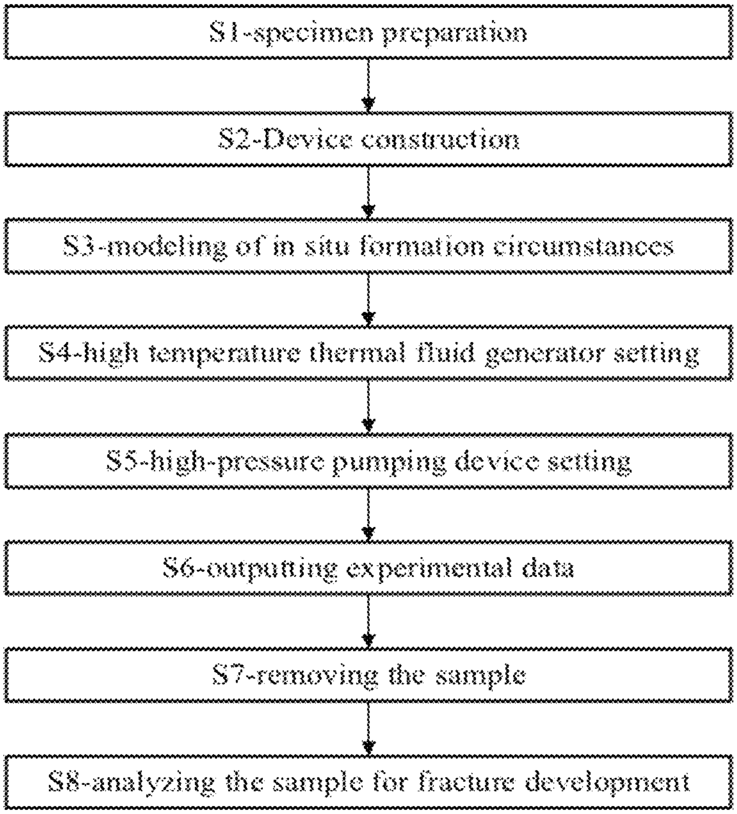

A third aspect of the present invention offers, with reference to FIGS. 2-3, an experimental approach for simulating the propagation of shale fractures under the influence of high-temperature convective heat, including the following steps:

S1, specimen preparation. A 100 mm×100 mm×100 mm typical shale sample 32 was prepared and drilled using a bench drill. The pre-processed simulated wellbore 19 is put into the shale sample 32, and epoxy resin glue is used for fixing and sealing.

S2, device construction. The shale sample 32 with the simulated wellbore 19 installed is put in the rock sealed cavity 33, followed by the sequential installation of the reaction kettle inner cavity cover 21 and reaction kettle outer cavity cover 20. The data collecting and processing system 1, the high-temperature thermal fluid generator 3, the high-pressure pump injection device 11 and the shale reaction kettle's 23 valves and pipes are then installed and linked.

S3, modeling of in situ formation circumstances. The parameters of the reactor temperature controller and the reactor triaxial confining pressure loader are set on the computer based on the required temperature and confining pressure of the experimental research, allowing the shale reaction kettle 23 to simulate and realize the in-situ conditions of the formation. By connecting the reactor temperature detector 28 and the reactor triaxial confining pressure detector to the data collecting module, the real-time experimental conditions of the reactor are monitored, the detection data is transmitted to the data collecting and processing system 1, and the data processing module records all relevant experimental data, X-axis confining pressure is 5 MPa, Y-axis confining pressure is 7 MPa, and Z-axis confining pressure is 10 MPa.

S4, high temperature thermal fluid generator 3 setting. Configure the temperature controller 5 and pressure controller 4 in order for the fluid generator 6 to create the thermal fluid conditions necessary for experimental research. In this example, it is configured to produce near-critical water with a fluid temperature of 350° C. and a pressure of 20 MPa.

S5, high-pressure pumping device 11 setting. A high-pressure constant-speed injection pump controller 10 regulates the injection flow rate and injection pressure of the high-temperature and high-pressure thermal fluid. Turn on the high-pressure constant-speed injection pump 12 to inject thermal fluid at a high temperature. During the experiment, the injection fluid temperature detector 17 measures the injection temperature in real time. The injection fluid pressure detector 15 monitors the injection pressure in real time during the experiment and communicates the detection data to the data collecting and processing system 1, where the data processing module captures and stores the pressure data. The injection flow rate of the thermal fluid is set at 10 ml/min in this case.

S6, outputting experimental data. Draw the temperature and pressure change curves over time using the temperature and pressure values acquired by the data collecting and processing system 1. Data storage and export for post-processing analysis.

S7, removing the sample. Unload the triaxial confining pressure loader at completion of the experiment. Close the reactor temperature controller 27, the fluid generator 6, and the high-pressure constant-speed injection pump 12. Remove the shale sample 32 once it has cooled.

S8, analyzing the sample for fracture development. Observe and assess the macroscopic fractures that have developed on the surface of the shale sample 32. Through CT scanning, the three-dimensional spatial distribution of fractures inside the rock sample was determined, and the fracture propagation pattern within the shale was seen.

It is important to note that the models and specifications of the data collecting and processing system 1, the high-temperature thermal fluid generator 3, the pressure controller 4, the temperature controller 5, the fluid generator 6, the high-pressure constant-speed injection pump controller 10, the high-pressure constant-speed injection pump 12, the injection fluid pressure detector 15, the injection fluid temperature detector 17, the triaxial confining pressure loader, the triaxial confining pressure detector, the reactor temperature controller 27 and the reactor temperature detector 28 must be chosen according to the apparatus's real characteristics. Since the particular type selection calculation approach utilizes existing technology, it will not be detailed in depth here.

It is important to note that the power supply and operating principle of the data collecting and processing system 1, the high-temperature thermal fluid generator 3, the pressure controller 4, the temperature controller 5, the fluid generator 6, the high-pressure constant-speed injection pump controller 10, the high-pressure constant-speed injection pump 12, the injection fluid pressure detector 15, the injection fluid temperature detector 17, the triaxial confining pressure loader, the triaxial confining pressure detector, the reactor temperature controller 27 and the reactor temperature detector 28 are well-understood by experts in the field and will not be explained in detail here.

The descriptions above are simply examples of preferred embodiments of the present invention, they are not meant to restrict the scope of the present invention. To those knowledgeable in the art, several changes and variants of the present invention will emerge naturally. Any changes, equivalent replacements, enhancements, etc. produced in accordance with the spirit and principles of the present invention are protected by the current patent.

What is claimed is:

1. An apparatus for simulating the propagation of shale fractures under high temperature convective heat, comprising:

a data collecting and processing system (1);

a high-temperature thermal fluid generator (3) comprising a fluid generator (6), a temperature controller (5), and a pressure controller (4), wherein an output end of the temperature controller (5) and an output end of the pressure controller (4) are electrically connected to an input end of the fluid generator (6);

a high-pressure pumping device (11) comprising a high-pressure constant-speed injection pump (12) and a high-pressure constant-speed injection pump controller (10), wherein an output end of the high-pressure constant-speed injection pump controller (10) is electrically connected to an input end of the high-pressure constant-speed injection pump (12), and wherein an output end of the data collecting and processing system is electrically coupled to an input end of the high-pressure constant-speed injection pump controller (10); and a shale reaction kettle (23) comprising a reaction kettle outer chamber (37), a reaction kettle outer cavity cover (20), a rock sealed cavity (33), and a shale sample (32), wherein the reaction kettle outer cavity cover (20) is positioned atop the reaction kettle outer chamber (37), the rock sealed cavity (33) is embedded in the reaction kettle outer chamber (37), the shale sample (32) is positioned within the rock sealed cavity (33), an inner net size of the rock sealed cavity (33) is the same as an external size of the shale sample (32), a reaction kettle inner cavity cover (21) is positioned over the rock sealed cavity (33), fastening bolts (22) are positioned atop the reaction kettle inner cavity cover (21) and screwed to a top of the rock sealed cavity (33), a reaction kettle base (38) is provided at a bottom of the reaction kettle outer chamber (37), a simulated wellbore (19) is placed on the reaction kettle outer cavity cover (20), a bottom end of the simulated wellbore (19) extends through the reaction kettle inner cavity cover (21) to the shale sample (32), and a top of the simulated wellbore (19) communicates with the high-pressure constant-speed injection pump (12).

2. The apparatus according to claim 1, wherein an output end of the fluid generator (6) is equipped with a connecting pipe (9), another end of the connecting pipe (9) is connected to the input end of the high-pressure constant-speed injection pump (12), and the connecting pipe (9) is equipped with an injection valve (8).

3. The apparatus according to claim 1, wherein an outlet end of the high-pressure constant-speed injection pump (12) is linked to a high-pressure pump injection pipe (14), a top of the simulated wellbore (19) is provided with a thread (18), and another end of the high-pressure pump injection pipe (14) is threadedly attached to the thread (18); the high-pressure pump injection pipe (14) is equipped with an injection valve (13), an injection fluid pressure detector (15), and an injection fluid temperature detector (17); and an output end of the injection fluid pressure detector (15) and an output end of the injection fluid temperature detector (17) are electrically connected to an input end of the data collecting and processing system (1), and the injection fluid pressure detector (15) is equipped with a first safety valve (16).

4. The apparatus according to claim 1, wherein an X-axis confining pressure loader (24), a Y-axis confining pressure loader (29), and a Z-axis confining pressure loader (34) are respectively disposed on a left side, a right side, and a bottom side of the reaction kettle outer chamber (37);

telescoping ends of the X-axis confining pressure loader (24), the Y-axis confining pressure loader (29), and the Z-axis confining pressure loader (34) contact the shale sample and penetrate a side wall of the rock sealed cavity (33);

output ends of the X-axis confining pressure loader (24), the Y-axis confining pressure loader (29), and the Z-axis confining pressure loader (34) are electrically connected to an X-axis confining pressure detector (26), a Y-axis confining pressure detector (30), and a Z-axis confining pressure detector (35), respectively; the X-axis confining pressure detector (26) has a second safety valve (25), the Y-axis confining pressure detector (30) has a third safety valve (31), and the Z-axis confining pressure detector (35) has a fourth safety valve (36);

input ends of the X-axis confining pressure loader (24), the Y-axis confining pressure loader (29), and the Z-axis confining pressure loader (34) are electrically connected to an output of the data collecting and processing system (1); output terminals of the X-axis confining pressure detector (26), the Y-axis confining pressure detector (30), and the Z-axis confining pressure detector (35) are electrically connected to an input terminal of the data collecting and processing system (1).

5. The apparatus according to claim 1, wherein an inner wall of the rock sealed cavity (33) is equipped with a reactor temperature controller (27) and a reactor temperature detector (28); an input end of the reactor temperature controller (27) is electrically connected to an output end of the data collecting and processing system (1); an output end of the reactor temperature detector (28) is electrically connected to an input end of the data collecting and processing system (1).

6. The apparatus according to claim 1, wherein the data collecting and processing system (1) comprises a computer, a data collecting module, and a data processing module; the computer is employed for the operation and management of the whole experiment; the data collecting module is used for real-time observation, simultaneous data collection, and experimental data display; and the data processing module is used for final data processing, export, and experiment storage.

7. An experimental approach for simulating the propagation of shale fractures under the influence of high-temperature convective heat, which is applied to the apparatus of claim 1, comprising the following steps:

S1, specimen preparation: drilling a 100 mm×100 mm×100 mm shale sample (32), placing a pre-processed simulated wellbore (19) into the shale sample (32), and using epoxy resin glue to fix the simulated wellbore (19) within the shale sample (32) and to seal an interface therebetween;

S2, device construction: placing the shale sample (32) with the simulated wellbore (19) installed into the rock sealed cavity (33), sequentially installing the reaction kettle inner cavity cover (21) and the reaction kettle outer cavity cover (20), and then installing and connecting the data collecting and processing system (1), the high-temperature thermal fluid generator (3), the high-pressure pumping device (11), and valves and pipes of the shale reaction kettle (23);

S3, modeling of in situ formation circumstances: parameters of a reactor temperature controller and a reactor triaxial confining pressure loader are set on a computer based on a required temperature and confining pressure of an experimental research, allowing the shale reaction kettle (23) to simulate and realize in-situ conditions of a formation, by connecting a reactor temperature detector (28) and a reactor triaxial confining pressure detector to a data collecting module, real-time experimental conditions of the reactor are monitored, a detection data is transmitted to the data collecting and processing system (1), and a data processing module records all relevant experimental data;

S4, high temperature thermal fluid generator (3) setting: configuring the temperature controller (5) and the pressure controller (4) in order for the fluid generator (6) to produce a thermal fluid required for experiment;

S5, high-pressure pumping device (11) setting: a high-pressure constant-speed injection pump controller (10) regulates the injection flow rate and injection pressure of the high-temperature and high-pressure thermal fluid, turn on the high-pressure constant-speed injection pump (12) to inject the thermal fluid, an injection fluid temperature detector (17) measures an injection temperature in real time, an injection fluid pressure detector (15) monitors the injection pressure in real time and communicates detection data to the data collecting and processing system (1), where the data processing module captures and stores pressure data;

S6, outputting experimental data: drawing temperature and pressure change curves over time using temperature and pressure values acquired by the data collecting and processing system (1), and storing and exporting data for post-processing analysis;

S7, removing the shale sample: unloading the triaxial confining pressure loader at completion of the experiment, closing the reactor temperature controller (27), the fluid generator (6), and the high-pressure constant-speed injection pump (12), and removing the shale sample (32) once it has cooled;

S8, analyzing the shale sample for fracture development: observing and assessing macroscopic fractures that have developed on a surface of the shale sample (32), determining a three-dimensional spatial distribution of fractures inside the shale sample (32) using CT scanning, and observing a fracture propagation pattern within the shale sample (32).

* * * * *